United States Patent
Harhen et al.

(10) Patent No.: US 7,540,846 B2
(45) Date of Patent: Jun. 2, 2009

(54) ENERGY APPLICATION WITH INFLATABLE ANNULAR LENS

(75) Inventors: Edward Paul Harhen, Duxbury, MA (US); Todd Fjield, Laguna Hills, CA (US); Patrick David Lopath, Stamford, CT (US); David E. Acker, St. James, NY (US)

(73) Assignee: ProRhythm, Inc., Ronkonkoma, NY (US)

( * ) Notice: Subject to any disclaimer, the term of this patent is extended or adjusted under 35 U.S.C. 154(b) by 566 days.

(21) Appl. No.: 11/267,123

(22) Filed: Nov. 4, 2005

(65) Prior Publication Data

US 2006/0058711 A1    Mar. 16, 2006

Related U.S. Application Data

(63) Continuation of application No. 09/904,963, filed on Jul. 13, 2001, now abandoned.

(60) Provisional application No. 60/218,641, filed on Jul. 13, 2000.

(51) Int. Cl.
*A61H 1/00* (2006.01)
*A61H 1/02* (2006.01)
*A61H 5/00* (2006.01)

(52) U.S. Cl. .................... 601/2; 601/3; 601/4; 600/437; 600/439; 606/27; 604/915; 604/103.14; 604/101.04

(58) Field of Classification Search ...... 601/2, 601/3, 4; 600/407, 437, 439; 606/27; 604/915, 604/103.14, 101.04
See application file for complete search history.

(56) References Cited

U.S. PATENT DOCUMENTS

| 3,168,659 A | 2/1965 | Bayre et al. |
| 4,084,582 A | 4/1978 | Nigam |
| 4,185,501 A | 1/1980 | Proudian et al. |
| 4,194,510 A | 3/1980 | Proudian |
| 4,387,720 A | 6/1983 | Miller |
| 4,391,281 A | 7/1983 | Green |
| 4,433,692 A | 2/1984 | Baba |

(Continued)

FOREIGN PATENT DOCUMENTS

EP    0 659 387 A    6/1995

(Continued)

OTHER PUBLICATIONS

Rappaport et al., "Wide-Aperture Microwave Catheter-Based Cardiac Ablation", Proceedings of the First Joint BMES/EMBS Conference, Oct. 13-16, 1999, p. 314.*

(Continued)

*Primary Examiner*—Eric F Winakur
*Assistant Examiner*—Katherine L Fernandez
(74) *Attorney, Agent, or Firm*—Lerner, David, Littenberg, Krumholz & Mentlik, LLP (57) ABSTRACT

Apparatus and methods for ablating tissue surrounding a tubular anatomical structure such as the wall of a blood vessel or prostatic tissue surrounding the urethra. The apparatus includes an ultrasonic emitter such as a cylindrical emitter and an inflatable annular lens balloon surrounding the ultrasonic emitter. The lens balloon is inflated with a liquid having acoustic velocity different than that of the surrounding medium, so as to form an annular refracting surface. The acoustic energy from the emitter is focused into an annular focal region.

12 Claims, 4 Drawing Sheets

U.S. PATENT DOCUMENTS

| | | | |
|---|---|---|---|
| 4,672,961 A | 6/1987 | Davies |
| 4,680,499 A | 7/1987 | Umemura et al. |
| 4,685,334 A | 8/1987 | Latimer |
| 4,691,714 A | 9/1987 | Wong et al. |
| 4,722,347 A | 2/1988 | Abrams et al. |
| 4,800,316 A | 1/1989 | Ju-Zhen |
| 4,841,977 A | 6/1989 | Griffith et al. |
| 4,869,263 A | 9/1989 | Segal et al. |
| 4,914,510 A | 4/1990 | Brennesholtz et al. |
| 4,945,912 A | 8/1990 | Langberg |
| 4,972,826 A | 11/1990 | Koehler et al. |
| 5,104,393 A | 4/1992 | Isner |
| 5,105,116 A | 4/1992 | Okamoto et al. |
| 5,117,831 A | 6/1992 | Jang et al. |
| 5,135,001 A | 8/1992 | Sinofsky et al. |
| 5,140,987 A | 8/1992 | Schuger |
| 5,160,336 A | 11/1992 | Favre |
| 5,167,233 A | 12/1992 | Eberle et al. |
| 5,209,299 A | 5/1993 | Ayres |
| 5,217,454 A | 6/1993 | Khoury |
| 5,226,421 A | 7/1993 | Frisbie et al. |
| 5,226,430 A | 7/1993 | Spears |
| 5,240,005 A | 8/1993 | Viebach |
| 5,242,438 A | 9/1993 | Saadatmanesh et al. |
| 5,242,441 A | 9/1993 | Avitall |
| 5,246,438 A | 9/1993 | Langberg |
| 5,281,213 A | 1/1994 | Milder et al. |
| 5,281,218 A | 1/1994 | Imran |
| 5,293,868 A | 3/1994 | Nardella |
| 5,295,484 A | 3/1994 | Marcus et al. |
| 5,305,731 A | 4/1994 | Buchholtz |
| 5,305,755 A | 4/1994 | Nakao |
| 5,364,388 A | 11/1994 | Koziol |
| 5,385,148 A | 1/1995 | Lesh et al. |
| 5,415,654 A | 5/1995 | Daikuzono |
| 5,419,335 A | 5/1995 | Hartmann et al. |
| 5,421,338 A | 6/1995 | Crowley et al. |
| 5,423,319 A | 6/1995 | Seyed-Bolorforosh |
| 5,423,807 A | 6/1995 | Milder |
| 5,454,782 A | 10/1995 | Perkins |
| 5,468,239 A | 11/1995 | Tanner |
| 5,471,988 A | 12/1995 | Fujio |
| 5,477,736 A | 12/1995 | Lorraine |
| 5,488,955 A | 2/1996 | Dias |
| 5,513,639 A | 5/1996 | Satomi et al. |
| 5,575,766 A | 11/1996 | Swartz et al. |
| 5,575,787 A | 11/1996 | Abela |
| 5,582,609 A | 12/1996 | Swanson et al. |
| 5,596,989 A | 1/1997 | Morita |
| 5,606,974 A | 3/1997 | Castellano |
| 5,620,479 A | 4/1997 | Diederich |
| 5,630,837 A | 5/1997 | Crowley |
| 5,655,539 A | 8/1997 | Wang et al. |
| 5,676,692 A | 10/1997 | Sanghui |
| 5,693,043 A | 12/1997 | Kittrell |
| 5,704,361 A | 1/1998 | Seward et al. |
| 5,707,352 A | 1/1998 | Sekins et al. |
| 5,720,287 A | 2/1998 | Chapelon et al. |
| 5,762,066 A | 6/1998 | Law et al. |
| 5,767,692 A | 6/1998 | Antonello et al. |
| 5,817,018 A | 10/1998 | Ohtomo |
| 5,840,031 A | 11/1998 | Crowley |
| 5,840,076 A | 11/1998 | Swanson et al. |
| 5,848,969 A * | 12/1998 | Panescu et al. ............... 600/462 |
| 5,860,974 A | 1/1999 | Abele |
| 5,916,170 A | 6/1999 | Kolz et al. |
| 5,916,213 A | 6/1999 | Haissaguerre et al. |
| 5,921,982 A | 7/1999 | Lesh et al. |
| 5,931,811 A | 8/1999 | Haissaguerre |
| 5,938,660 A | 8/1999 | Swartz et al. |
| 5,964,751 A | 10/1999 | Amplatz |
| 5,971,983 A | 10/1999 | Lesh |
| 6,002,955 A | 12/1999 | Willems |
| 6,004,269 A | 12/1999 | Crowley et al. |
| 6,012,457 A | 1/2000 | Lesh |
| 6,013,053 A | 1/2000 | Bower et al. |
| 6,022,319 A | 2/2000 | Willard |
| 6,024,740 A | 2/2000 | Lesh et al. |
| 6,055,859 A | 5/2000 | Kozuka et al. |
| 6,064,902 A | 5/2000 | Haissaguerre |
| 6,068,629 A | 5/2000 | Haissaguerre et al. |
| 6,071,279 A | 6/2000 | Whayne |
| 6,094,988 A | 8/2000 | Aindow |
| 6,106,474 A | 8/2000 | Koger et al. |
| 6,117,101 A | 9/2000 | Diederich et al. |
| 6,146,379 A | 11/2000 | Fleischman |
| 6,152,144 A | 11/2000 | Lesh et al. |
| 6,152,920 A | 11/2000 | Thompson |
| 6,161,543 A | 12/2000 | Cox et al. |
| 6,163,716 A | 12/2000 | Edwards |
| 6,164,283 A | 12/2000 | Lesh |
| 6,166,092 A * | 12/2000 | Sekins et al. ............... 514/772 |
| 6,190,382 B1 | 2/2001 | Ormsby |
| 6,193,713 B1 | 2/2001 | Geistert et al. |
| 6,196,059 B1 | 3/2001 | Kosslinger et al. |
| 6,197,023 B1 | 3/2001 | Muntermann |
| 6,200,269 B1 | 3/2001 | Lin et al. |
| 6,200,315 B1 | 3/2001 | Gaiser et al. |
| 6,203,525 B1 | 3/2001 | Whayne |
| 6,203,531 B1 | 3/2001 | Ockuly et al. |
| 6,206,831 B1 | 3/2001 | Suorsa |
| 6,212,426 B1 | 4/2001 | Swanson |
| 6,231,561 B1 | 5/2001 | Frazier |
| 6,235,025 B1 | 5/2001 | Swartz et al. |
| 6,237,605 B1 | 5/2001 | Vaska et al. |
| 6,241,754 B1 | 6/2001 | Swanson et al. |
| 6,245,064 B1 | 6/2001 | Lesh et al. |
| 6,251,109 B1 | 6/2001 | Hassett et al. |
| 6,254,599 B1 | 7/2001 | Lesh et al. |
| 6,280,402 B1 | 8/2001 | Ishibashi et al. |
| 6,282,949 B1 | 9/2001 | Axelsson |
| 6,283,127 B1 | 9/2001 | Sterman et al. |
| 6,290,674 B1 | 9/2001 | Roue et al. |
| 6,305,378 B1 | 10/2001 | Lesh |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,778 B1 | 11/2001 | Gambale et al. |
| 6,330,473 B1 | 12/2001 | Swanson et al. |
| 6,332,880 B1 | 12/2001 | Yang et al. |
| 6,383,151 B1 | 5/2002 | Diederich et al. |
| 6,398,792 B1 | 6/2002 | O'Connor |
| 6,461,314 B1 | 10/2002 | Pant |
| 6,492,762 B1 | 12/2002 | Pant et al. |
| 6,500,174 B1 | 12/2002 | Maguire et al. |
| 6,513,385 B1 | 2/2003 | Han et al. |
| 6,517,536 B2 | 2/2003 | Hooven et al. |
| 6,543,274 B1 | 4/2003 | Herrmann et al. |
| 6,642,515 B1 | 11/2003 | Yamaguchi |
| 6,652,515 B1 | 11/2003 | Maguire et al. |
| 2001/0007070 A1 | 7/2001 | Stewart et al. |
| 2002/0065512 A1 | 5/2002 | Fjield et al. |
| 2003/0050637 A1 | 3/2003 | Maguire et al. |

FOREIGN PATENT DOCUMENTS

| | | |
|---|---|---|
| EP | 1042990 | 10/2000 |
| WO | WO-90/00420 | 1/1990 |
| WO | WO-98/41178 | 9/1998 |
| WO | WO-98/49957 | 11/1998 |
| WO | WO-98/52465 | 11/1998 |
| WO | WO-99/02096 | 1/1999 |
| WO | WO-99/44519 | 9/1999 |
| WO | WO-99/52423 | 10/1999 |

| WO | WO-00/16850 | 3/2000 |
| WO | WO-00/27292 | 5/2000 |
| WO | WO-00/42934 | 7/2000 |
| WO | WO-00/51511 | 9/2000 |
| WO | WO-00/51683 | 9/2000 |
| WO | WO-00/56237 | 9/2000 |
| WO | WO-00/67648 | 11/2000 |
| WO | WO-00/67656 | 11/2000 |
| WO | WO-00/67830 | 11/2000 |
| WO | WO-00/67832 | 11/2000 |

OTHER PUBLICATIONS

Krimholtz et al., "New Equivalent Circuits for Elementary Piezoelectric Transducers," Electronics Lettres, vol. 6, No. 13, pp. 398-399, Jun. 25, 1970.

Kumagai, Koichiro, "Treatment of Mixed Atrial Fibrillation and Typical Atrial Flutter by Hybrid Catheter Ablation," 2000.

Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 47 (1999) (Suppl.) 347-51.

Lesh, Michael D., M.D., "Radiofrequency Catheter Ablation of Atrial Arrhythmias," 1994.

Liem, L. Bing, "In Vitro and In Vivo Results of Transcatheter Microwave Ablation Using Forward-Firing Tip Antenna Design," 1996.

Lin, Wei-Shiang, M.D., "Pulmonary Vein Morphology in Patients with Paroxysmal Atrial Fibrillation Initiated by Ectopic Beats Originating From the Pulmonary Veins," Circulation 101(11):1274-81, 2000.

Mallavarapu, Christopher, "Radiofrequency Catheter Ablation of Atrial Tachycardia with Unusual Left Atrial Sites of Origin," 1996.

Montenero, Sandro, Annibale, "Electrograms for Identification of the Atrial Ablation Site During Catheter Ablation of Accessory Pathways," 1996.

Moubarak, Jean B., "Pulmonary Veins-Left Atrial Junction: Anatomic and Histological Study," Pacing & Clin. Electrophys. 23(11 pt. 2):1836-8, 2000.

O'Connor, Brian K., "Radiofrequency Ablation of A Posteroseptal Accessory Pathway Via the Middle Cardia Vein in a Six-Year Old Child," 1997.

Partial Supplementary European Search Report, Application No. EP 01 95 2750, Filed Sep. 16, 2005.

Prager, Nelson, A., "Long Term Effectiveness of Surgical Treatment of Ectopic Atrial Tachycardia," 1993.

Reuter, David, M.D., "Future Directions of Electrotherapy for Atrial Fibrilation," 1997.

Robbins, Ivan, M.D., "Pulmonary Vein Stenosis After Catheter Ablation of Atrial Fibrillation," 1998.

Scheinman, Melvin M., "NASPE Survey on Catheter Ablation," 1995.

Swartz, John F., "A Catheter-based Curative Approach to Atrial Fibrillation in Humans," 1994.

Swartz, John F., M.D., "Radiofrequency Endocardial Catheter Ablation of Accessory Atrioventricular Pathway Atrial Insertion Sites," 1993.

Tracy, Cynthia M., "Radiofrequency Catheter Ablation of Ectopic Atrial Tachycardia Using Paced Activation Sequence Mapping," J. of the Amer. College of Cardiol. 21(4):910-7, 1993.

Van Hare, George F., "Radiofrequency Catheter Ablation of Supraventricular Arrhythmias in Patients With Congenital Heart Disease: Results and Technical Considerations," J. of the Amer. College of Cardiol. 22(3):883-90, 1993.

Volkmer, Marius, M.D., "Focal Atrial Tachycardia from Deep Inside the Pulmonary Veins," 1997.

Walsh, Edward P., M.D., "Transcatheter Ablation of Ectopic Atrial Tachycardia in Young Patients Using Radiofrequency Current," 1992.

Zipes, Douglas P., M.D., "Catheter Ablation of Arrhythmias," 1994.

\* cited by examiner

ENERGY APPLICATION WITH INFLATABLE ANNULAR LENS

CROSS-REFERENCE TO RELATED APPLICATIONS

The present application is a continuation of U.S. patent application Ser. No. 09/904,963, filed Jul. 13, 2001, which application claims the benefit of the filing date of U.S. Provisional Patent Application No. 60/218,641, filed Jul. 13, 2000, the disclosures of which are hereby incorporated by reference herein.

FIELD OF THE INVENTION

The present application relates to medical procedures such as hyperthermia, and to apparatus adapted for use these and other procedures.

BACKGROUND OF THE INVENTION

In certain medical procedures, it is desirable to heat tissue surrounding a tubular anatomical structure such as a blood vessel or a gastrointestinal, urinary, genital, or respiratory structure. Depending upon the condition to be treated, energy may be applied to the tissue constituting the wall of the structure, or to tissue surrounding the wall. Energy may be applied to heat the tissue to a degree sufficient to cause death of the tissue. Heating to this degree is referred to herein as "ablation." Typically, heating to about 60-80° C. is sufficient.

For example, the prostate, which surrounds the urethra in males, may become enlarged and constrict the urethra. To relieve this condition, the tissue of the prostate gland can be ablated.

Also, contraction or "beating" of the heart is controlled by electrical impulses generated at nodes within the heart and transmitted along conductive pathways extending within the wall of the heart. Certain diseases of the heart known as cardiac arrhythmias involve abnormal generation or conduction of the electrical impulses. One such arrhythmia is atrial fibrillation or "AF." Certain cardiac arrhythmias can be treated by deliberately damaging the tissue of the cardiac wall along a path crossing a route of abnormal conduction. This causes formation of a scar extending along the path where disruption occurred. The scar blocks conduction of the electrical impulses. The abnormal electrical impulses can be carried by abnormal structures extending within the wall of a pulmonary vein. Conduction of these abnormal electrical impulses may be blocked by forming a scar in the wall of the pulmonary vein or in the opening or ostium of the pulmonary vein.

For example, as described in *Lesh*, International Publication WO 99/02096, such ablation can be performed by threading a catheter having a thermal ablation element at its distal tip into the heart so that the tip is lodged within the appropriate pulmonary vein. The catheter may bear a balloon which is inflated within the vein and which holds the catheter in place. The ablating element is then actuated so as to apply heat in a region surrounding the ablating element. In certain embodiments taught in the '096 publication, the ablating element includes a radio frequency ("RF") emitting element which is carried on the surface of the balloon. Ablation of the pulmonary vein using RF energy can create a rough, disrupted surface on the interior of the vein. This or other factors can lead to stenosis of the pulmonary vein or thrombosis, i.e., formation of blood clots.

Other embodiments described in the '096 publication disclose the use of ultrasonic transducers. The preferred ultrasonic transducer illustrated in the '096 publication is a rigid ceramic piezoelectric element disposed on a catheter surrounded by a balloon. When the balloon is inflated, the piezoelectric element remains remote from the wall of the pulmonary vein. The piezoelectric element can be actuated to apply sonic energy through a fluid contained in the balloon, thereby heating the ring of vein wall tissue surrounding the balloon. As a further alternative, the '096 publication shows an ultrasonic emitter in the form of a hollow concave disk. The '096 publication suggests that such an emitter can be physically rotated around the axis of a catheter so as to ablate a ring-like zone. These transducers have numerous drawbacks.

Ultrasonic heating such as high intensity focused ultrasound (HIFU) is utilized for many therapeutic applications. As disclosed in commonly assigned International Application PCT/US98/1062, published as International Publication WO/98/52465, the disclosure which is hereby incorporated by reference herein, HIFU heating typically is conducted using an ultrasonic emitter having an array of transducers. The transducers are actuated with a drive signal so as to emit ultrasonic waves. The relative phasing of the waves is controlled by the physical configuration of the array and the phasing of the drive signal. These factors are selected so that the ultrasonic waves tend to reinforce one another constructively at a focal location. Tissue at the focal location is heated to a greater extent than tissue at other locations. As described, for example in U.S. patent application Ser. No. 09/496,988, filed Feb. 2, 2000, now U.S. Pat. No. 6,461,314; and in U.S. patent application Ser. No. 09/532,614, filed Mar. 22, 2000, now U.S. Pat. No. 6,492,762, the disclosures of which are also incorporated by reference herein, HIFU may be applied by transducer arrays such as arrays of polymeric piezoelectric transducers. These arrays can be mounted on a probe such as a catheter which can be introduced into the body as, for example, within the vascular system or into a cavernous internal organ. The '988 application discloses certain transducer arrays which can be deformed so as to vary the placement of the focal location.

Crowley, U.S. Pat. No. 5,630,837 discloses a probe carrying an ultrasonic transducer array including multiple cylindrical elements spaced apart from one another along a common axis. The probe can be inserted into an anatomical structure and actuated to form an annular lesion surrounding the transducer array. The ultrasonic energy is focused into an annular focal region by phasing the ultrasonic waves emitted from the individual cylindrical elements.

Despite all of these efforts in the art, there have been needs for further improvements in the devices and methods used to apply thermal energy to tissue surrounding tubular anatomical structures. In particular, it would be desirable to provide simple apparatus which can apply intense energy in a ring or annulus around a tubular structure, and which can tightly control the zone of energy application. There have been corresponding needs for further improvement in the devices and methods used to apply energy to other organs of the body for thermal treatment.

SUMMARY OF THE INVENTION

One aspect of the invention provides apparatus for applying energy to tissue within the body of a living subject as, for example, tissues surrounding the wall of a tubular anatomical structure. Apparatus according to this aspect of the invention includes an ultrasonic emitter having an emitting surface generally in the form of a surface of revolution about a central axis and an inflatable lens surrounding the ultrasonic emitter. The lens has a refractive surface generally in the form of a surface of revolution about the central axis when the lens is inflated. In operation, at least some of the ultrasonic energy, and preferably most or all of the ultrasonic energy emitted at the emitting surface will be directed through the refracted surface of the lens and directed into an annular region surrounding the central axis. The annular region most preferably has an axial extent less than the axial extent of the emitting surface. The power emitted over substantially the entire axial extent of the emitting surface will be directed into the annular region and thus focused in the annular region to provide effective thermal treatment. Focusing the energy promotes rapid heating and minimizes collateral damage to the neighboring tissues.

The apparatus may include a structure adapted to engage the wall of the tubular anatomical structure and hold the emitter at a predetermined location relative to the anatomical structure, preferably at the center of the anatomical structure so that the focal region is precisely located relative to the wall of the anatomical structure. The structure for holding the emitter may include a bearing balloon surrounding the lens and the emitter. Desirably, the bearing balloon, when inflated, has a predetermined shape. The inflatable lens and the bearing balloon are provided with separate ports so that different fluids, having substantially the same acoustic impedance but having different acoustic velocities, can be introduced into the lens and the bearing balloon to inflate them. Typically, the bearing balloon in its inflated condition is also in the form of a surface of revolution such as a cylinder and the emitter and lens are coaxial with the bearing balloon. The bearing balloon may be arranged to stretch the anatomical structure slightly so as to bring the wall of the anatomical structure to a precise, round shape coaxial with the lens and emitter and thereby position the lens and emitter precisely relative to the wall. In other embodiments, the lens itself engages and distends the wall of the anatomical structure and thus acts to hold the emitter in precise relationship to the wall of the anatomical structure.

The lens and emitter may be arranged to place the focal region within the wall or other tissue surrounding the tubular structure, so that the ultrasonic energy comes to a focus in the tissue rather than at the surface of the wall. Placing the focus within the tissue, rather than at the surface of the tissue, minimizes scarring at the surface and also promotes rapid heating.

Alternatively, the apparatus may be arranged to direct sonic energy outwardly from the focal region in a collimated generally disc-shaped pattern. As described in detail below, this requires at least two interfaces. The first interface, at the surface of the lens, refracts the ultrasonic waves axially inwardly, toward the plane of an annular focal region, whereas the second interface refracts the inwardly directed to a substantially radially direction. Such a radial, collimated pattern provides relatively high sonic intensity over a substantial depth into the surrounding tissue. This facilitates formation of a thermally treated region having sufficient depth as, for example, an ablated region extending entirely through the wall of a pulmonary vein or the pulmonary vein ostium to assure reliable interruption of the abnormal conductive paths present in atrial fibrillation. A radially-extensive pattern also facilitates ablation or other thermal treatment where the anatomical structure is not precisely round or where the lens and the emitter cannot be positioned precisely concentric with the anatomical structure.

A related aspect of the invention provides methods of treating tissue surrounding tubular anatomical structure. Methods according to this aspect of the invention include the steps of positioning an elongated emitter having an emitting surface in the form of a surface of revolution about a central axis and a lens having a refracting surface in the form of a surface of revolution concentric with the emitter surface so that the emitter and lens are substantially concentric with the tubular anatomical structure, and actuating the emitter to emit sonic energy so that the sonic energy is directed into a substantially annular region, concentric with the lens and emitter and hence substantially concentric with the anatomical structure. Most preferably, the annular region has axial extent substantially smaller than the axial extent of the emitter.

As discussed above in connection with the apparatus, focusing of the sound into an annular region of a relatively small axial extent concentrates the sonic energy and permits efficient and precise thermal treatment. In particular, concentration of the sonic energy into a relatively small axial region facilitates rapid heating of a ring-like portion of tissue surrounding the anatomical structure. This facilitates ablation or other thermal treatment in such a ring-like region and helps to limit undesired heating of adjacent tissues. Methods according to this aspect of the invention can be used for ablation of the pulmonary vein or pulmonary vein ostium to treat atrial fibrillation, for treatment of the prostate, and for other conditions.

Other objects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Apparatus according to one embodiment of the invention (FIGS. 1 and 2) includes a probe structure 710 incorporating a single multi-lumen catheter 716. A first fitting 705 at the proximal end of the catheter communicates with lumen 701 whereas another fitting 707 at the proximal end of the catheter communicates with lumen 703. An emitting element 720 having an emitting surface generally in the form of a surface of revolution is mounted to catheter 716 adjacent the distal end 709 of the catheter. The emitting element defines a medial plane 721 perpendicular to central axis 724 midway between the proximal and distal ends of the emitting element. A bearing balloon 711 surrounds the emitting element. The bearing balloon is formed from a flexible material such as a polymer. Materials similar to those used to form noncompliant balloons in the angioplasty art, such as films of PET, PETG, nylon, polyurethane, polyethylene and other polymers can be used. Typically, such balloons are inflated to a relatively high preselected inflation pressure, referred to herein as the "design inflation pressure," such as a few atmospheres to 10 or 12 atmospheres. Inflation pressures of this order render the balloon relatively rigid. Stated another way, the balloon will assume a predictable, preselected shape when inflated to the design inflation pressure, with minimal deviation from this shape despite variations in external pressure applied by the surrounding blood and soft tissue. The balloon wall desirably has the minimum thickness required to withstand the design inflation pressure without rupturing, as, for example, about 0.001 inches (1 mil) or less, preferably about 0.5 mils or less.

Figure 1:
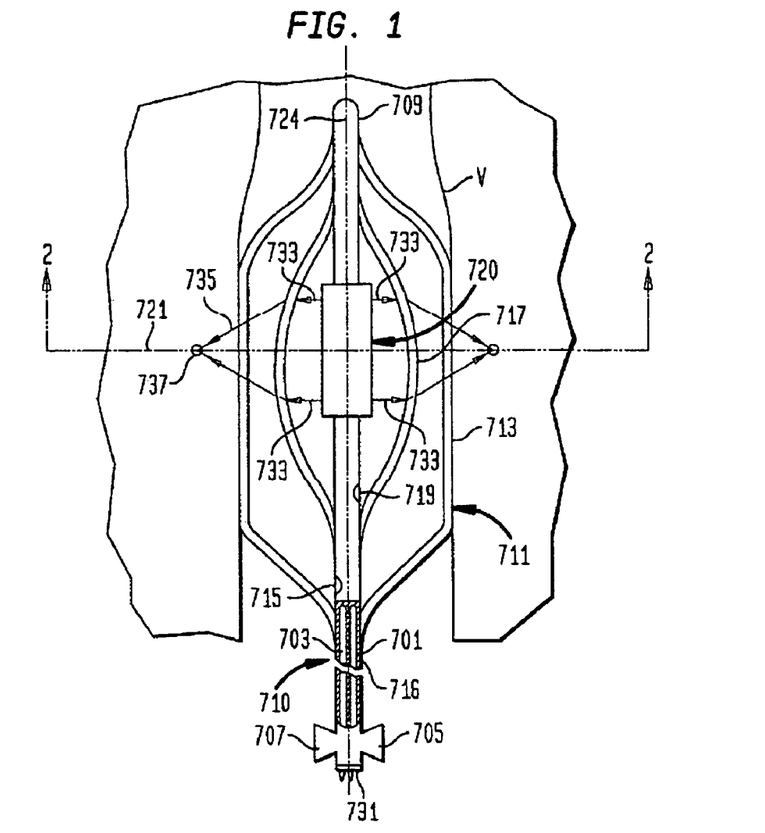
FIG. 1 is a fragmentary diagrammatic view depicting apparatus according to a further embodiment of the invention in conjunction with a blood vessel.
Figure 2:
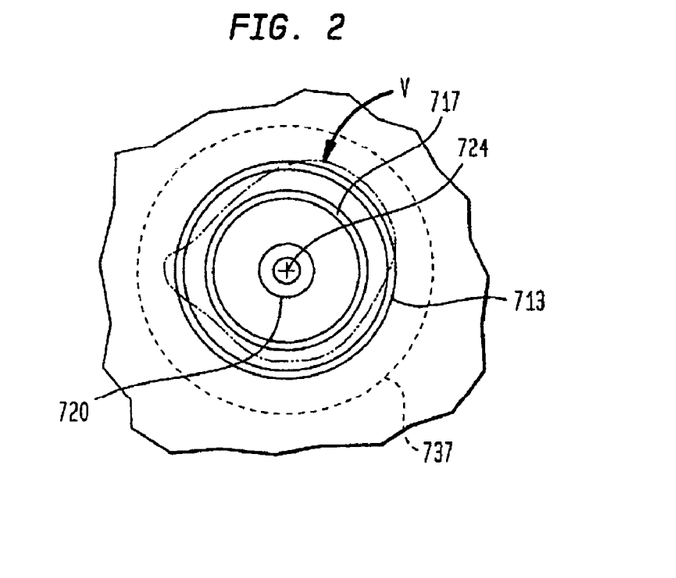
FIG. 2 is a diagrammatic sectional view taken along line 2-2 in FIG. 1.

In its inflated configuration, the bearing balloon has a substantially cylindrical wall section 713 coaxial with the central axis 724 of the emitting element. The bearing balloon communicates with lumen 703 through a port 705. A lens balloon 717 surrounds the emitting element 720 within bearing balloon 711. The lens balloon also has a preselected shape in a fully inflated condition. The preselected shape of the lens balloon is surface of revolution about central axis 724, concentric with the cylindrical section of bearing balloon 713 and with the cylindrical emitting element 720. The lens balloon is convex. That is, the generatrix forming the surface of revolution defined by the lens balloon has its greatest radius adjacent the medial plane 721 of the emitting element. The interior of lens balloon 717 is connected to lumen 701 by a port 719.

In a method according to a further embodiment of the invention, the distal end of the catheter is advanced into the body of a living subject while the balloons are in a deflated condition. This advancement is continued until the emitting element and balloons are disposed within a tubular anatomical structure such as a blood vessel as, for example, a pulmonary vein in a subject suffering from atrial fibrillation. In its normal state, the pulmonary vein V typically is not precisely round. For example, the vein may have the cross-sectional shape indicated by dot-dash lines in FIG. 10. Lens balloon 717 is inflated by passing a fluid having acoustic velocity less than that of aqueous fluids but having acoustic impedance close to that of an aqueous fluid as, for example, a fluorocarbon, into the balloon through fitting 705, lumen 701 and port 719. Bearing balloon 711 is inflated with an aqueous fluid such as water or saline.

In the fully inflated condition, the cylindrical section 713 of bearing balloon 711 has a circumference larger than the normal, undistended circumference of the vein V. Therefore, inflation of bearing balloon 711 distends the vein slightly and places the vein wall V in close, intimate contact with the bearing balloon around the entire cylindrical section 713. The amount of distention is not critical. The distention desirably is sufficient to assure contact between the bearing balloon's cylindrical surface 713 and the vein wall at all points, but desirably not so great as to damage the vein wall. Typically, the circumference of the bearing balloon in its inflated condition is selected to be about 5% to about 10% greater than the normal, undistended circumference of the vein wall. Because the bearing balloon has a preselected shape with its cylindrical surface disposed at a known, predetermined distance from the central axis 724, the central axis and hence the emitting element 720 and lens balloon 717 are positioned at precise distances from the vein wall, and are concentric with the vein wall, when the bearing balloon is inflated. Emitting element 720 is actuated, as by applying signals to a connector 731 at the proximal end of the probe structure so that such signals can be conducted to the emitting element through conductors (not shown) carried in or along the probe structure. Once again, the emitting element emits substantially cylindrical ultrasonic waves which propagate substantially radially as indicated by arrows 733 in FIG. 9. These waves are refracted at the interface formed by the different fluids in lens balloon 717 and bearing balloon 713 and bent towards the medial plane 721 as indicated by arrows 735 and hence focused into an annular focal region 737 concentric with central axis 724. Because the central axis is concentric with the distended vein wall, the focal region lies at a substantially equal distance to the vein wall around the entire circumference of the vein. Stated another way, the focal region is disposed at a substantially equal depth within the vein tissue at all points around the circumference of the vein. Moreover, the acoustic waves will be coupled efficiently into the tissue at the interface between the bearing balloon and the vein wall. Therefore, the tissue will be heated evenly throughout the circumference of the vein. Because the acoustic power from the entire emitting element 720 is focused into a small focal region 737, tissue in and around the focal region is heated rapidly, so that ablation or other thermal treatment can be performed with only minimal heating of other tissues.

Although the foregoing discussion refers to ablation of the vein wall, it should be appreciated that the technique discussed above with reference to FIGS. 10 and 11 can be applied to ablation of the ostium and to the transition region between the ostium and the vein itself. The ostium is composed entirely of myocardial tissue, whereas the vein is composed entirely of vein tissue except for abnormal strands of myocardial tissue in the case of patients suffering from atrial fibrillation. These abnormal strands act as electrical initiators or triggers to produce ectopic beats, i.e., disorganized beats. The transition region includes both myocardial and vein tissue. Whether the ablation is conducted in the ostium, in the transition region or in the vein, it is normally regarded as desirable to provide complete transmural ablation, i.e., to ablate tissue entirely through the wall so as to be certain that the abnormal strands are ablated or fully isolated from the myocardial tissue of the heart by a barrier of scar tissue.

The apparatus and methods can be used for purposes other than ablation of tissues of the heart and circulatory vessels. For example, any tubular internal organ can be treated in a manner similar to that described above to ablate the tissue surrounding the interior of the organ. In a condition referred to as gastroesophageal reflux disease or "GERD," abnormal tissues within the esophagus or stomach may be treated by positioning apparatus as discussed above within the stomach and/or within the esophagus and ablating the abnormal tissue. Also, the techniques discussed above can be used to treat tissues surrounding other tubular anatomical structures as, for example, structures of the digestive system, respiratory system or urinary system.

In a further preferred method, the apparatus can be employed to treat benign prostatic hyperplasia ("BPH"). In this condition, the prostate gland surrounding the urethra in a male subject swells and tends to constrict the urethra. The apparatus may be inserted into the urethra and ultrasonic energy may be directed into a ring-like focal region outside of the urethra, within the surrounding prostatic tissue so as to ablate the prostate and relieve the swelling. The radial distance from the central axis of the apparatus to the focal region may be selected so as to place the focal region either within the prostate itself or within the capsule surrounding the prostate.

Figure 3:
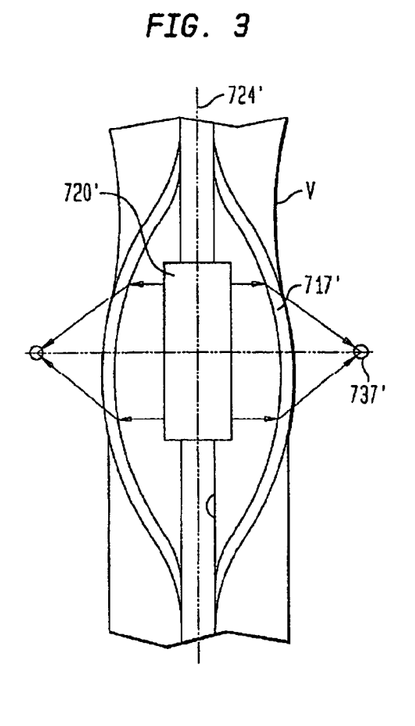
FIGS. 3, 4, 5 and 6 are views similar to FIG. 1, but depicting apparatus according to further embodiments of the invention.
Figure 4:
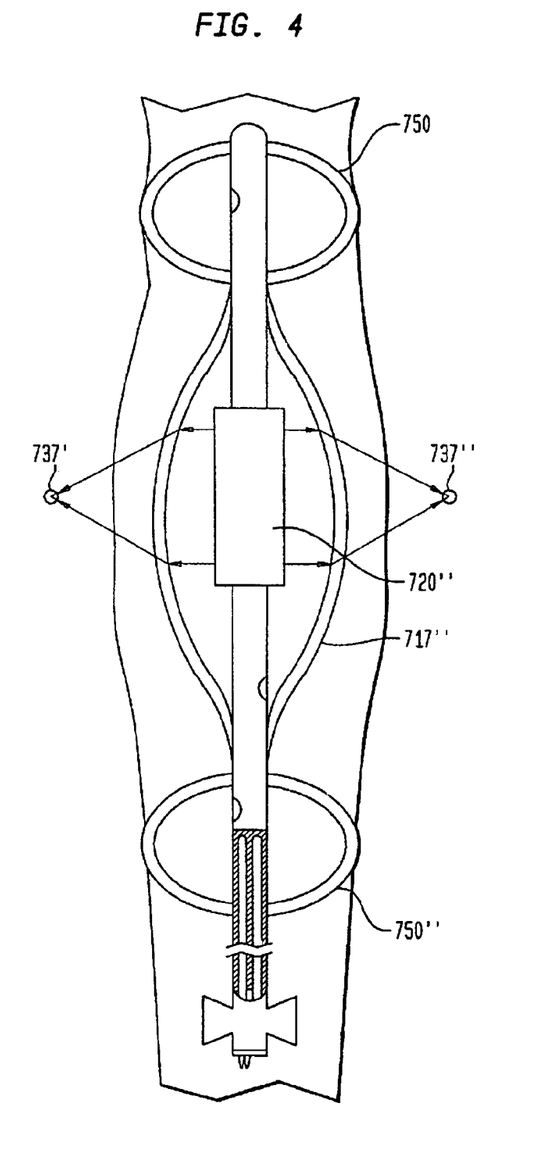

As shown in FIG. 3, the bearing balloon may be omitted. The lens balloon instead bears directly on the vein wall V. Because the lens balloon has a predetermined shape and size, it precisely locates the central axis 724' of the emitting element 720' and distends the tissue in substantially the same way as discussed above with respect to the bearing balloon of FIGS. 1 and 2. Here again, the lens balloon is filled with a fluid such as a fluorocarbon or other liquid having acoustic velocity lower than that of aqueous fluids but having acoustic impedance close to that of an aqueous fluid. The tissue of the vein wall has acoustic properties similar to those of water and other aqueous fluids. Accordingly, refraction of the acoustic waves occurs at the interface between lens balloon 717' and the vein wall tissue, so that the acoustic waves will be focused into a focal region 737' in a manner similar to that discussed above with reference to FIGS. 1 and 2. In a further variant (FIG. 4), the lens balloon 717", emitting element 720" and hence the central axis 724" may be held at a location substantially concentric with the vein wall by centering structures such as additional balloons 750 and 751, umbrella-like structures or other expansible structures disposed adjacent the lens balloon, so that the lens balloon does not bear on the vein wall. In this arrangement, the refraction occurs at the interface between the fluid within the lens balloon 717" and the surrounding blood within the vein. In this arrangement, the vein wall may remain in its non-circular state during application of ultrasonic energy and hence the depth of focal region 737" within the tissue may vary somewhat. In a further variant, the space between the lens balloon and the vein wall may be filled with another fluid as, for example, saline solution.

Apparatus according to a further embodiment of the invention (FIG. 5) includes an emitting element 820, lens balloon 817 and an outer balloon 811 generally similar to the corresponding elements discussed above with reference to FIGS. 1 and 2. However, the preselected shape of lens balloon in its inflated condition includes a surface of revolution 801 which is substantially concentric with the emitting element and central axis 824, but which has a concave shape. That is, the generatrix of surface of revolution 801 has its smallest radius or distance from axis 824 at a location adjacent the medial plane 821 of emitting element 820, and surface 801 curves radially outwardly in axial directions away from this medial plane. The outer balloon 811 in its inflated condition has a similar concave surface of revolution 813. In use, the assembly is positioned within a tubular anatomical structure such as a vein. The outer balloon 811 is filled with a fluid having acoustic velocity less than the acoustic velocity of aqueous fluids, whereas the lens balloon is filled with an aqueous fluid or another fluid having acoustic velocity greater than that of the fluid in the outer balloon. In a manner similar to that discussed above, the emitting element is actuated to emit substantially cylindrical ultrasonic waves which propagate generally radially outwardly as indicated by arrows 833. Here again, the acoustic waves are refracted axially inwardly towards an annular focus 837 on the medial plane 821 at the interface between the lens balloon and the bearing balloon due to the difference in acoustic velocities between the fluids contained in these balloons. However, because the fluid in outer balloon 811 has an acoustic velocity lower than the acoustic velocity of the surrounding blood or other fluid in the anatomical structure, the acoustic waves are refracted again at the interface between the outer balloon and the surrounding tissues. This refraction directs the waves substantially radially, so that the waves propagate generally parallel to one another and generally radially as indicated by arrows 839 in a generally disc-shaped pattern. Thus, the acoustic waves effectively irradiate a deep, annular region. The depth of penetration of the acoustic waves is limited only by attenuation of the waves as they are absorbed by the tissue. In this arrangement, the acoustic waves are not focused to a point or line, but nonetheless are effectively concentrated within a relatively narrow axial region. This arrangement can provide effective heating even if the central axis of the apparatus is not precisely coaxial with the vein.

Figure 5:
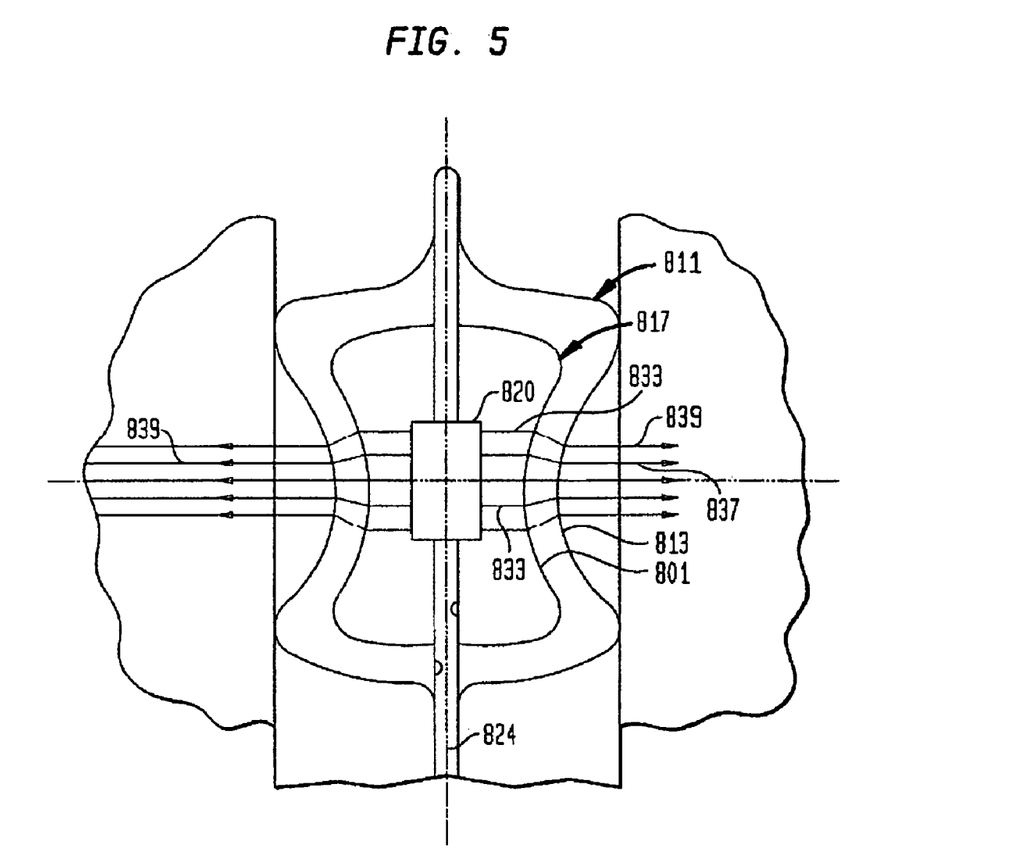
Figure 6:
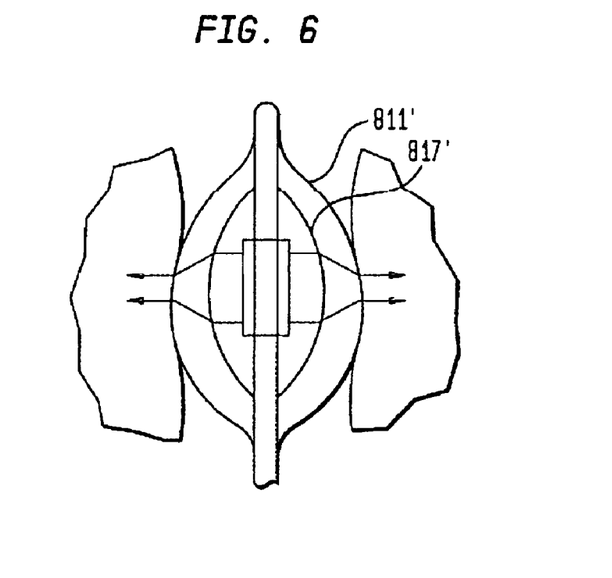

In the embodiment of FIG. 5, regions of the outer balloon remote from the medial plane 821 contact the vein wall. However, this is not essential. The entire assembly may be held adjacent the center of the vein by auxiliary positioning structures as discussed above with reference to FIG. 4. In a directly analogous arrangement, (FIG. 6) the lens balloon 817' is convex, and filled with an aqueous fluid. The outer balloon 811' is also convex but is filled with a fluid having acoustic velocity higher than that of water.

In the embodiments discussed above, the apparatus acts to direct the applied energy into an annular region. However, in further embodiments of the invention, the reflector structure may direct the energy into a region of a different shape.

Thermal treatments other than ablation can be performed. For example, hyperthermia can be applied to potentiate the action of a drug or other agent in a particular region of the body.

Also, the particular liquids and other materials mentioned above can be replaced by other materials having similar properties. In a further variant, the focal depth can be varied by varying the inflation pressures within the various balloons. To provide greater variation in configuration with variations in pressure, more readily distensible materials such as elastomeric materials may be used to form the refractive regions of the balloons. In yet another variant, the focal length of an inflatable lens can be adjusted while maintaining the shape of the lens constant by varying the composition of the fluid in the lens or the fluid in a surrounding balloon.

In additional variants, the liquids, which are used to inflate the balloons in the embodiments discussed above, can also serve as temperature control media. The source of liquid used to inflate a balloon may include a pump for circulating the liquid into the interior space of the balloon through one lumen and withdrawing the liquid through the other lumen while maintaining the liquid in the balloon under the desired pressure. The liquid source can be arranged to provide the liquid at a desired temperature. In this way, the thermal boundary condition at the wall of the anatomical structure is well controlled. The controlled temperature may be below normal body temperature to keep the interface cool and minimize or prevent ablation of epithelial cells lining the anatomical structure. Conversely, a higher boundary temperature will promote ablation at or near the surface of the wall. To maximize this effect, the fluid in the bearing balloon may be maintained just below the temperature which will cause tissue damage independently of the ultrasonic energy as, for example, up to about 41° C. Similar arrangements can be employed in the other embodiments. Liquid circulation also serves to cool the ultrasonic element. For example, the liquid in the lens balloon can be circulated and temperature-controlled.

Figures 9, 10:
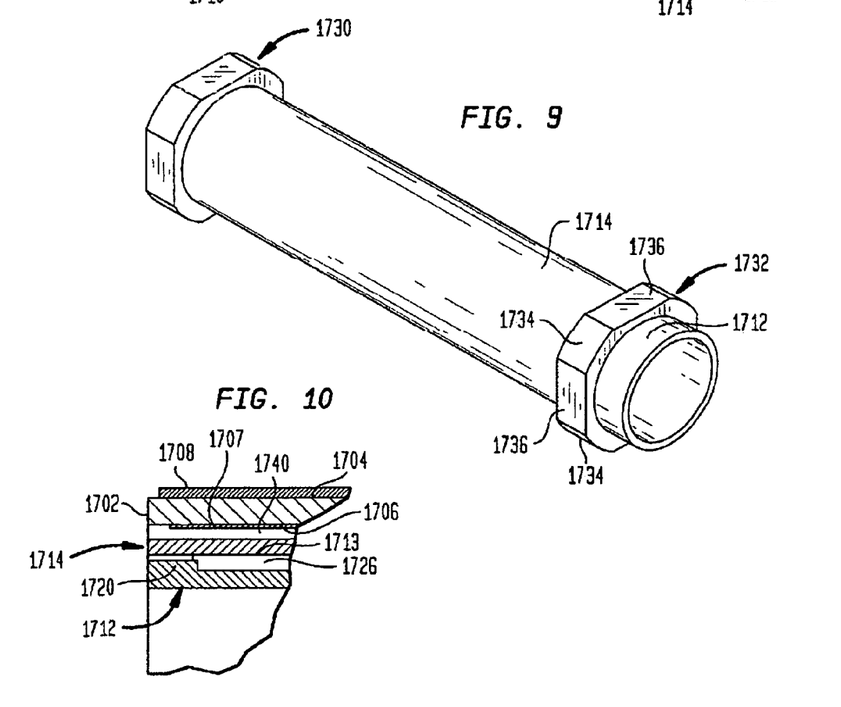
FIG. 9 is a perspective view of a part of the transducer of FIGS. 7 and 8.
FIG. 10 is a fragmentary view on an enlarged scale of the area indicated in FIG. 8.

A preferred ultrasonic transducer or emitter usable in the present invention is depicted in FIGS. 7-10. This transducer is further described in U.S. patent application Ser. No. 09/904, 620, entitled "Ultrasonic Transducers," filed Jul. 13, 2001, now U.S. Pat. No. 6,763,722, the disclosure of which is hereby incorporated by reference herein. The emitter includes an active piezoelectric element 1702 in the form of a thin cylindrical tube having an exterior or front surface 1704 and an interior or rear surface 1706. An electrode 1708 forms the front surface 1704 of the piezoelectric element, and a similar electrode 1707 forms the rear surface. The thickness of the electrode is greatly exaggerated in FIGS. 20 and 22 for clarity of illustration. In practice, the electrode preferably is formed by a thin metallic coating, such as a plated or sputtered coating of metal on the order of a few thousand Angstroms thick overlying the actual piezoelectric material. An internal structure 1710 includes an inner support tube 1712 and an outer support tube 1714. Support tubes 1712 and 1714 desirably are formed from a metallic, electrically conductive material. As best seen in FIG. 10, inner support tube 1712 has an outwardly projecting shoulder 1720 at one end. A similar shoulder 1722 is provided at the opposite end. Outer support tube 1714 has a cylindrical internal bore. Shoulders or rings 1720 and 1722 fit closely within the cylindrical bore of the outer support tube. Thus, over the major portion of the length of the support structure, between shoulders 1720 and 1722, there is a gap 1726 between the inner surface of outer support tube 1714 and the outer surface of inner support tube 1712. The tubes are sealed to one another at shoulders 1720 and 1722. Gap 1726 is filled with a gas, such as normal room air, at the time the tubes are sealed to one another. This gas remains permanently within gap 1726.

Figure 7:
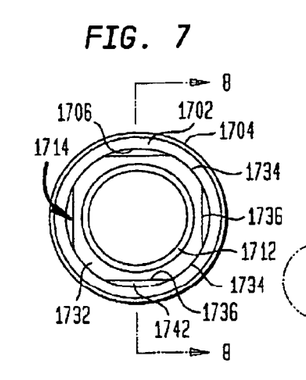
FIG. 7 is an end view of a transducer used in an embodiment of the invention.
Figure 8:
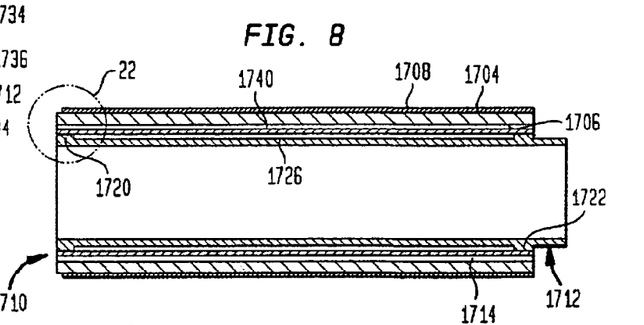
FIG. 8 is a sectional view of the transducer of FIG. 7.

Outer support tube 1714 has a pair of outwardly projecting shoulders 1730 and 1732 at the ends of the outer support tube. Each shoulder has arcuate surfaces 1734 connected by flats 1736, so that each shoulder is generally in the form of a square with rounded corners. The arcuate surfaces 1734 are concentric with the main portion of the support tube 1714. Seen in end view, the flats 1736 are tangent to the cylindrical surface of the main portion of the support tube. As best seen in FIG. 7, the tubular piezoelectric electric element 1702 is supported on the arcuate surfaces 1734 of shoulders 1732 and 1730, so that the inner surface 1706 of the piezoelectric element is concentric with the outer surface of support tube 1714, but is spaced apart from the support tube so as to define a space in the form of a tubular passageway 1740 between the outer support tube and the inner or rear surface 1706 of the piezoelectric element. Passageway 1740 is open to the exterior of the transducer through small gaps 1742 defined between the inner surface 1706 of the piezoelectric element and the flats 1736 of the shoulders on the outer support tube.

In operation, the space or passageway 1740 is filled with a liquid. The front surface of the emitter (the front surface 1704 of the active piezoelectric element) is acoustically coupled to the medium which is to receive ultrasonic energy from the emitter.

For example, the emitter of FIGS. 7-10 may be used as the ultrasonic emitter apparatus of depicted in FIG. 1. In this case, the liquid within lens balloon 717 will be present as the acoustic medium at the front surface of the emitter, and will fill passageway 1740. Desirably, the source of lens fluid circulates this liquid so that the liquid moves through passageway 1740.

The air or other gas in gap 1726 (FIGS. 8, 10) forms a highly-reflective interface 1713 with the metallic material of the outer support tube 1714. In operation, the emitter is excited by an electrical potential applied between electrodes 1707 and 1708. This potential is applied at a predetermined ultrasonic drive frequency as, for example, about 1-15 MHz. The potential may be applied through electrical conductors (not shown) extending between the proximal end of the probe structure and the emitter, using a conventional ultrasonic-frequency driver (not shown). For example, the conductors may be provided as one or more miniature coaxial cables, each including an inner conductor and an outer conductor or jacket. The jackets of the coaxial cables may be soldered or otherwise bonded to the outer support tube, and hence electrically connected to the inner-surface electrode of the piezoelectric element, whereas the inner conductors may be connected to the outer-surface electrode 1708.

The reflective interface at surface 1713 (FIG. 10) and the outer surface 1704 of the emitter, and the stack of materials between these surfaces, constitute a resonant unit. As the piezoelectric material is excited, it repeatedly grows and shrinks in the forward-to-rearward direction of the stack, i.e., in the direction between surfaces 1704 and 1706. The ultrasonic vibrations propagate through the stack, and are reflected forwardly at the interfaces within the stack and by the interface at surface 1713, at the inner or rear surface of the stack. The dimensions of the various layers in the interior of the stack, between surfaces 1713 and 1704 (including the liquid layer within space 1740) are selected so that the unit is resonant at the drive frequency, and so that the acoustic vibrations are emitted from the resonant unit principally through the front surface 1704 into the medium coupled to the front surface. That is, more energy passes through the interface 1704 at the outer or front surface of the stack than through interface 1713. Although there is some reflectivity at interfaces within the stack, as at the interfaces bounding the liquid passageway 1740, the reflective interface 1713 is effectively exposed to the ultrasonic vibrations in the stack and, thus, plays a substantial role in directing emissions to the front of the stack. The liquid within passageway 1740 effectively cools the piezoelectric element and other elements of the stack. Thus, the transducer element 1702 is cooled at both its front surface and its rear surface. This is in marked contrast to a conventional air-backed transducer. Such a transducer typically has a layer of air directly behind the rear surface of the piezoelectric element and, accordingly, has little or no heat transfer from the rear surface of the piezoelectric element. Surprisingly, an emitter in accordance with this design can convert electrical power to acoustic power radiated into the surrounding medium through the front surface with an efficiency equal to the efficiency of an air-backed emitter. The emitter according to this design, however, provides this efficiency in conjunction with better heat transfer and, hence, can operate at substantially higher power levels than the equivalent air-backed transducer of the same size.

The materials and dimensions of the various layers in the resonant unit desirably are optimized to assure maximum efficiency at the desired operating frequency. Conventional modeling techniques may be employed for such optimization. One such technique is the well-known KLM Model described in Krimholtz et al., "New Equivalent Circuits for Elementary Piezoelectric Transducers," Electronics Letters, Vol. 6, No. 13, pp. 398-399, Jun. 25, 1970, the disclosure of which is hereby incorporated by reference herein. The various layers can be modeled as one-dimensional elements, with the only dimension corresponding to the dimension in the forward-to-rearward direction of the stack, i.e., the radial dimension in the embodiment of FIGS. 19-22. More precise optimization can be provided by finite element analysis and/or physical modeling and testing. In the emitter of FIGS. 25-28, the liquid in space or passageway 1740 forms an integral part of the resonant unit.

The inner support tube provides a passage through the emitter for catheters, guidewires or other elements of the apparatus. The inner support tube, and any elements disposed within it, are effectively isolated from the ultrasonic vibrations in the resonant unit by reflective interface 1713, and therefore do not affect performance of the emitter.

The optimum dimensions will vary with the desired operating frequency and with the materials employed. However, one exemplary embodiment uses a tubular piezoelectric element made from a ceramic lead zirconate-titanate composition, known in the art by the designation "PZT-8." The tubular transducer has an internal diameter of 83 mils (0.083 inches; 2.1 mm) and a wall thickness of 10.5 mils (0.27 mm), so that the outer diameter of the piezoelectric element is 103 mils (2.6 mm). The outer diameter of outer support tube 1714 is 72 mils (1.8 mm); and the annular passageway 1740 has a radial thickness of 5.5 mils (0.14 mm). The outer support tube is formed from half-hard brass and has a wall thickness of 5 mils (0.13 mm). The dimension between shoulders 1720 and 1722 is 325 mils (8.25 mm), and the effective length of the transducer is 8 mm. This transducer provides peak efficiency at a driving frequency of 9 MHz. When operated at 9 MHz, the transducer provides over fifty percent (50%) efficiency at electrical power levels between 20 and 100 watts. When cooled by water flowing at a rate of a few ml per minute, the transducer has been operated for periods of several minutes or more at power levels up to 100 watts to provide approximately 51 watts of radiated acoustic power.

The apparatus discussed above can be varied. For example, the apparatus can be used to apply ultrasonic energy in structures other than internal organs of living subjects. Also, the transducer used as an emitter also serves as a receiver in an ultrasonic imaging application. Thus, the transducer can be actuated intermittently and then used to detect echoes from structures surrounding the apparatus. The apparatus may be arranged to provide a radially-directed radiation pattern such as that discussed with reference to FIG. 5. Such apparatus can be used, for example, in an intravascular ultrasound procedure or in other medical applications, or in non-medical applications such as in inspection of pipes or tubes. The apparatus can be moved along the length of a structure to scan the radiating ultrasound along the length of the structure.

The ultrasonic emitter discussed above can be replaced by an optical emitter as, for example, a fiber optic having a distal end disposed within the lens balloon and a proximal end connected to an external light source. The fiber optic is provided with a lens or conical mirror at its distal end to direct light radially outwardly. In this modification, the fluids in the balloons are selected to provide different optical indices of refraction, rather than to provide different acoustic velocities.

The apparatus also may include structures for placing the balloons and facilitating orderly collapse of the balloons as described in the copending, commonly assigned U.S. patent application Ser. No. 09/905,227, entitled "Thermal Treatment Methods And Apparatus With Focused Energy Application," filed Jul. 13, 2001, now U.S. Pat. No. 6,635,054, the disclosure of which is hereby incorporated by reference herein. Other features disclosed in such application also can be employed.

As these and other variations and combinations of the features discussed above can be employed, the foregoing description of the preferred embodiments should be taken by way of illustration rather than by way of limitation of the invention.

The invention claimed is:

1. Apparatus for applying ultrasonic energy to tissue within the body of a living subject comprising:
  (a) an ultrasonic emitter having an emitting surface extending around a central axis and facing outwardly away from said central axis;
  (b) an inflatable lens, said lens having a refractive surface extending around said central axis when said lens is in an inflated condition, said lens surrounding said emitter so that at least some ultrasonic energy emitted at said emitting surface will be directed through said refractive surface of said lens into the tissue of the subject, and said ultrasonic energy is focused by said lens into a region having axial extent smaller than the axial extent of said emitter, said refractive surface in said inflated condition defining an interface between media having different acoustic velocities.

2. Apparatus as claimed in claim 1, further comprising an elongated probe, said probe having a proximal end and a distal end adapted for insertion into the body of a living subject, said emitter and said inflatable lens being mounted to said probe adjacent the distal end thereto.

3. Apparatus as claimed in claim 2, further comprising a reflector structure including a first balloon defining an active region and a second balloon disposed adjacent said first balloon and contiguous with said first balloon over at least a part of said active region, so that said first and second balloons can be inflated with fluids having different acoustic impedances so as to form a reflective interface at said active region.

4. Apparatus as claimed in claim 1, wherein said inflatable lens is adapted to focus ultrasonic energy emitted by said emitter into an annular focal region surrounding said central axis.

5. Apparatus as claimed in claim 4, further comprising a bearing balloon surrounding said emitter and said lens, said bearing balloon having a bearing surface adapted to engage the wall of an organ of the subject.

6. Apparatus as claimed in claim 5, wherein said bearing balloon is operative to engage the interior surface of the wall of a tubular organ, so that said annular focal region lies along a ring-like path on said wall.

7. Apparatus as claimed in claim 6, wherein said bearing balloon is operative to engage the interior surface of a pulmonary vein.

8. Apparatus as claimed in claim 5, wherein said probe includes a first lumen communicating with said bearing balloon and a second lumen communicating with said inflatable lens so that said bearing balloon and said lens can be inflated with fluids having substantially similar acoustic impedances but different acoustic velocities, whereby the ultrasonic energy will be refracted at said refractive surface.

9. Apparatus as claimed in claim 1 wherein said emitting surface is a surface of revolution about said central axis and said refractive surface is a surface of revolution about said central axis when said lens is in said inflated condition.

10. A method for applying ultrasonic energy to tissue surrounding a tubular internal organ of a living subject comprising:
  (a) inserting an ultrasonic emitter having an emitting surface extending around a central axis and an inflatable lens surrounding said emitter into the interior of said organ; and
  (b) inflating said lens so as to bring said lens to a configuration having a refractive surface substantially extending around said central axis and extending around said emitting surface, said lens configured for focusing said ultrasonic energy into a region having axial extent smaller than the axial extent of said emitter, said inflating step being performed so that said refractive surface in said configuration defines an interface between media having different acoustic velocities; and
  (c) actuating said emitter to emit ultrasonic energy so that said ultrasonic energy passes outwardly away from said axis through said lens, said ultrasonic energy is refracted at said refractive surface, and said ultrasonic energy is concentrated by said lens into a region having axial extent smaller than the axial extent of the emitter.

11. A method as claimed in claim 10, further comprising providing an additional refractive interface surrounding said lens so that the concentrated ultrasonic energy is refracted again at said additional refractive interface and propagates substantially radially from said additional refractive interface.

12. A method as claimed in claim 10 wherein said inserting step includes providing said emitting surface as a surface of revolution about said central axis and step of inflating said lens includes providing said refractive surface in said configuration as a surface of revolution about said central axis.

* * * * *